(12) United States Patent
Grott et al.

(10) Patent No.: US 10,882,037 B2
(45) Date of Patent: Jan. 5, 2021

(54) APPARATUS AND PROCESS FOR CONTACTING CATALYST WITH A GAS AND REDUCTION

(71) Applicant: UOP LLC, Des Plaines, IL (US)

(72) Inventors: Jeffrey R. Grott, Chicago, IL (US); Michael J. Vetter, Schaumburg, IL (US); Jennifer J. Ozmen, Chicago, IL (US); Quan Yuan, Buffalo Grove, IL (US)

(73) Assignee: UOP LLC, Des Plaines, IL (US)

( * ) Notice: Subject to any disclaimer, the term of this patent is extended or adjusted under 35 U.S.C. 154(b) by 386 days.

(21) Appl. No.: 15/685,644

(22) Filed: Aug. 24, 2017

(65) Prior Publication Data

US 2018/0117580 A1    May 3, 2018

Related U.S. Application Data

(60) Provisional application No. 62/414,529, filed on Oct. 28, 2016.

(51) Int. Cl.
| | |
|---|---|
| *B01J 38/04* | (2006.01) |
| *B01J 8/12* | (2006.01) |
| *B01J 8/08* | (2006.01) |
| *C07C 2/42* | (2006.01) |
| *B01D 53/96* | (2006.01) |
| *C07C 5/393* | (2006.01) |

(52) U.S. Cl.
CPC ............. *B01J 38/04* (2013.01); *B01D 53/96* (2013.01); *B01J 8/085* (2013.01); *B01J 8/12* (2013.01); *B01J 8/125* (2013.01); *C07C 2/42* (2013.01); *C07C 5/393* (2013.01)

(58) Field of Classification Search
CPC ...... B01J 38/04; B01J 8/085; B01J 8/08–085; B01J 8/12; B01J 8/125
See application file for complete search history.

(56) References Cited

U.S. PATENT DOCUMENTS

| | | | |
|---|---|---|---|
| 4,687,637 A | 8/1987 | Greenwood | |
| 5,167,795 A | 12/1992 | Gartside et al. | |
| 7,262,147 B2 | 8/2007 | Steigleder et al. | |
| 7,951,341 B2 | 5/2011 | Stewart et al. | |
| 2002/0151757 A1* | 10/2002 | Boehner | B01J 27/16 585/350 |
| 2013/0221123 A1 | 8/2013 | Oshinowo et al. | |
| 2015/0098862 A1 | 4/2015 | Lok et al. | |
| 2015/0224464 A1 | 8/2015 | Grott et al. | |

OTHER PUBLICATIONS

PCT Search Report dated Dec. 21, 2017 for corresponding PCT Application No. PCT/US2017/052483.
Written opinion from corresponding PCT application No. PCT/US2017/052483, dated Dec. 11, 2017.
Search Report from corresponding PCT application No. PCT/US2017/052483, dated Dec. 21, 2017.
International Preliminary Report on Patentability from corresponding PCT application No. PCT/US2017/052483, dated Apr. 30, 2019.

* cited by examiner

*Primary Examiner* — Anthony J Zimmer
*Assistant Examiner* — Syed T Iqbal

(57) ABSTRACT

A process and apparatus is disclosed for distributing a gas stream into a downwardly flowing catalyst stream in a vessel by feeding the gas stream into a center of the vessel or the catalyst stream into a hollow cap. The gas stream enters the cap and exits the cap flowing upwardly to contact the catalyst stream.

11 Claims, 1 Drawing Sheet

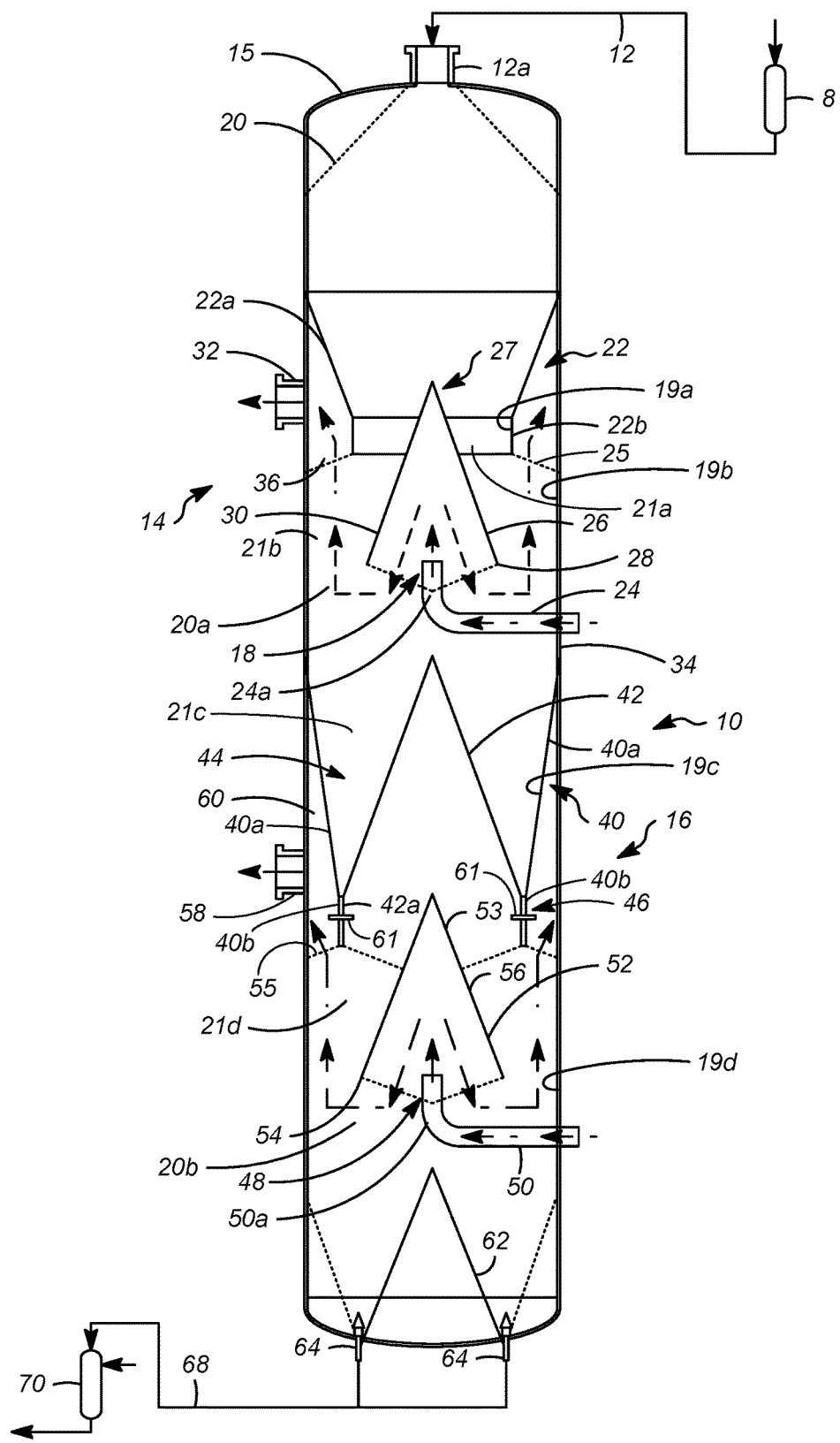

APPARATUS AND PROCESS FOR CONTACTING CATALYST WITH A GAS AND REDUCTION

CROSS-REFERENCE TO RELATED APPLICATION

This application claims priority from Provisional Application No. 62/414,529 filed Oct. 28, 2016, the contents of which cited application are hereby incorporated by reference in its entirety.

FIELD

The present subject matter relates generally to methods for contacting a catalyst stream for catalytic conversion with a gas. More specifically, the present subject matter relates to methods for drying and reducing a catalyst for reuse in the hydrocarbon conversion process.

BACKGROUND

Hydrocarbon reaction processes typically involve contacting streams of particulates such as catalyst with gaseous streams either for conversion of the gaseous stream or treatment of the catalyst such as by regeneration. In such contacting regimes, it is important to assure sufficiently thorough contact between the catalyst stream and the gaseous stream. Thorough distribution requires sufficient pressure drop through the catalyst stream or bed to ensure the gas permeates the entire cross section of the catalyst stream or bed.

Hydrocarbon processes such as dehydrocyclodimerization utilize a catalyst comprising metal on zeolitic material comprising aluminum silicates. Metals on the dehydrocyclodimerization catalyst must be in the reduced state in the reaction zone to be effective. However, the catalyst accumulates coke in the reaction zone that must be oxidized to remove coke from the catalyst in an oxidative regeneration zone. Hence, after oxidative regeneration, the catalyst must be reduced before entering the dehydrocyclodimerization reactor by contact with hydrogen gas to reduce the metals on the catalyst. The zeolite can dealuminate in the presence of water at high temperature. Dealumination can destabilize the structure and effectiveness of the catalyst.

Hydrothermal dealumination accounts for the majority of catalyst deactivation over the life of the dehydrocyclodimerization catalyst. The propensity of zeolitic materials to dealuminate increases as water concentration and temperature increase. Sources of water include desorption of water on the catalyst coming from the oxidative regeneration section and water generated in the high temperature reduction zone in the presence of a hydrogen reducing gas. A preferred level of reduction necessitates high temperature which inevitably desorbs a substantial amount of chemisorbed water contributing to hydrothermal damage of the catalyst. In addition, any remaining chemisorbed water on the catalyst returning to the reactor will desorb in the reactor in which the catalyst spends a significant amount of residence time at elevated temperature. Both the reduction zone and the dehydrocyclodimerization reactor contribute to hydrothermal dealumination since both zones may have high water partial pressure and temperature.

In addition to loss of activity due to coke formation, catalysts containing a phosphorus modified alumina as a binder are gradually deactivated over a period of time from several months to about a year by exposure to hydrogen at temperatures generally greater than 500° C. (932° F.) and particularly greater than 565° C. (1049° F.). This loss of activity due to hydrogen exposure cannot be restored by oxidative regeneration.

Therefore, improvement of the reduction zone design can significantly reduce hydrothermal catalyst damage in both the reduction zone and the dehydrocyclodimerization reactor.

SUMMARY

The present subject matter comprises a process of distributing a gas stream into a downwardly flowing catalyst stream in a vessel by feeding the gas stream into a center of the vessel or the catalyst stream into a hollow cap. The gas stream enters the cap and exits the cap flowing upwardly to contact the catalyst stream.

The present subject matter also comprises an apparatus for distributing a gas stream into a catalyst stream comprising an inlet for introducing the catalyst stream to a vessel and a pipe for feeding a gas stream to a center of a catalyst passage in the vessel. The pipe has an outlet end directed into a cap. The vessel has a catalyst exit in a lower end of the vessel and a gas outlet is in a side of the vessel.

The present subject matter also comprises a reduction process comprising feeding a catalyst stream comprising water downwardly in a vessel while feeding a first gas stream into a center of the catalyst stream into a hollow cap. The first gas stream enters the cap and exits the cap flowing upwardly to contact and dry the catalyst stream that is flowing downwardly to provide a dried catalyst stream and a wet gas stream. The wet gas stream is discharged through a first side outlet from the vessel. A second gas stream is fed to the vessel to contact the dried catalyst stream to reduce the valence state of metals in the dried catalyst stream to provide a reduced catalyst stream and a used gas stream. The reduced catalyst stream and the used gas stream are discharged from the vessel.

Feeding the drying gas stream to the center of the catalyst stream produces acceptable gas distribution within the catalyst stream while minimizing catalyst residence time. The centered inlet produces a higher pressure drop necessary for thorough gas distribution without the need for an excessive catalyst flow rate or bed volume.

Definitions

As used herein, the term "dehydrocyclodimerization" is also referred to as aromatization of light paraffins. Within the subject disclosure, dehydrocyclodimerization and aromatization of light hydrocarbons are used interchangeably. As used herein, the term "stream", "feed", "product", "part" or "portion" can include various hydrocarbon molecules, such as straight-chain, branched, or cyclic alkanes, alkenes, alkadienes, and alkynes, and optionally other substances, such as gases, e.g., hydrogen, or impurities, such as heavy metals, and sulfur and nitrogen compounds. The stream can also include aromatic and non-aromatic hydrocarbons. Moreover, the hydrocarbon molecules may be abbreviated $C_1$, $C_2$, $C_3$, Cn where "n" represents the number of carbon atoms in the one or more hydrocarbon molecules or the abbreviation may be used as an adjective for, e.g., non-aromatics or compounds. Similarly, aromatic compounds may be abbreviated $A_6$, $A_7$, $A_8$, An where "n" represents the number of carbon atoms in the one or more aromatic molecules. Furthermore, a superscript "-" may be used with an abbreviated one or more hydrocarbons notation, e.g., $C_{3-}$, which refers to molecules that contain less than or equal to x and preferably x and less carbon atoms. Moreover, a superscript "+" may be used with an abbreviated one or more hydrocarbons notation, e.g., $C_{3+}$, which refers to molecules with more than or equal to x and preferably x and more carbon atoms. As an example, the abbreviation "$C_{3+}$" means one or more hydrocarbon molecules of at least three or more carbon atoms and preferably three or more carbon atoms.

As used herein, the term "zone" can refer to an area including one or more equipment items and/or one or more sub-zones. Equipment items can include, but are not limited to, one or more reactors or reactor vessels, separation vessels, distillation towers, heaters, exchangers, pipes, pumps, compressors, and controllers. Additionally, an equipment item, such as a reactor, dryer, or vessel, can further include one or more zones or sub-zones.

As used herein, the term "active metal" can include metals selected from IUPAC Groups that include 6, 7, 8, 9, 10, 13 and mixtures of thereof. The IUPAC Group 6 trough 10 includes without limitation chromium, molybdenum, tungsten, rhenium, platinum, palladium, rhodium, iridium, ruthenium, osmium, zinc, copper, and silver. The IUPAC Group 13 includes without limitation gallium and indium.

As used herein, the term "modifier metal" can include metals selected from IUPAC Groups 11-17. The IUPAC Group 11 trough 17 includes without limitation sulfur, gold, tin, germanium, and lead.

The term "communication" means that material flow is operatively permitted between enumerated components.

The term "downstream communication" means that at least a portion of material flowing to the subject in downstream communication may operatively flow from the object with which it communicates.

The term "direct communication" means that flow from the upstream component enters the downstream component without undergoing a compositional change due to physical fractionation or chemical conversion.

BRIEF DESCRIPTION OF THE DRAWING

The FIGURE depicts one or more implementations in accord with the present concepts, by way of example only, not by way of limitations. In the FIGURE, like reference numerals refer to the same or similar elements.

The FIGURE is a schematic depiction of a vessel.

DETAILED DESCRIPTION

We have found that locating a gas inlet in the center of the catalyst stream or bed provides unexpected advantages for contacting a particulate stream with a gas that has a very low gas density. Surprisingly, a side inlet does not work for contacting a particulate stream with a gas that has a very low gas density, such as below 0.3 kg/m³ (0.02 lb/ft³) at operating conditions. A side distributor would require a higher pressure drop to achieve the requisite distribution with a gas stream that has a low gas density such as hydrogen. Distribution can be improved by adding additional catalyst volume, but this would cause additional contact time between the catalyst and hydrogen which is not desirable especially with a catalyst that deactivates from prolonged hydrogen exposure such as a dehydrocyclodimerization catalyst.

The following detailed description is merely exemplary in nature and is not intended to limit the application and uses of the embodiment described. Furthermore, there is no intention to be bound by any theory presented in the preceding background or the following detailed description.

The FIGURE illustrates a flow diagram typical of various embodiments of the processes and apparatuses described herein. Those skilled in the art will recognize that this flow diagram has been simplified by the elimination of many pieces of process equipment including for example, heat exchangers, process control systems, pumps, fractionation column overhead, reboiler systems and reactor internals, etc. which are not necessary to an understanding of the process. The description relates to a reduction vessel but the disclosed subject matter may be applied to any apparatus or process for contacting particulates with gas.

With reference to the FIGURE, an apparatus and process in accordance with various embodiments includes a reduction vessel 10. A stream of regenerated catalyst particles in a regenerated catalyst line 12 is continuously fed from a regenerator vessel 8 to the reduction vessel 10. The catalyst particles may be introduced at a top 15 of the reduction vessel 10 through a catalyst inlet 12*a* and flow downwardly through the reduction vessel 10 as a catalyst stream 20. The regenerated catalyst line 12 is in downstream communication with the regeneration vessel 8 which by oxidatively combusting hydrocarbonaceous coke from the catalyst particles generates water which may be chemisorbed on the catalyst particles. The catalyst stream has a minimum of 0.1 wt % chemisorbed water.

Although the term continuous is applied to this process herein, the process may include a continuous, semi-continuous, or batch process where small amounts of catalyst are withdrawn from the regenerator vessel 8 and passed to the reduction vessel 10 on a relatively continuous basis. As catalyst particles flow down through the reduction vessel 10, a peripheral boundary of the catalyst stream 20 eventually conforms to a cross sectional shape defined by an inner passageway through the vessel 10. In an aspect, the inner configuration of the reduction vessel 10 is cylindrical, thus providing generally cylindrical passageways. The catalyst stream 20 passes through passageways 19*a*, 19*b*, 19*c* and 19*d* of varying inner diameters to provide catalyst beds 21*a*, 21*b*, 21*c* and 21*d*. The catalyst beds are typically cylindrical, although other cross sectional shapes of the catalyst beds are contemplated.

Upper and lower boundaries of the catalyst beds are shown with dotted lines and gas flow currents are shown by dashed lines in the FIGURE.

The reduction vessel 10 may be divided into an upper drying zone 14 and a lower reduction zone 16. A first annular baffle 22 has an inclined, annular upper wall 22*a* and an optional lower annular, vertical wall 22*b*. The first annular baffle 22 defines a first passageway 19*a* that is of reduced inner diameter while descending in the first passageway 19*a* until reaching the elevation of the lower vertical wall 22*b*. The catalyst stream 20 descends through the first passageway 19*a* in the drying zone 14 of the reduction vessel 10 to consolidate the catalyst stream 20 into a first catalyst bed 21*a* which may be cylindrical and of smaller diameter than above the first annular baffle 22. In an aspect, the first annular baffle 22 is impermeable to solids and fluid flow. However, the first annular baffle 22 may be made permeable to vapor flow. After descending past the annular baffle 22, the catalyst stream expands into a second passageway 19*b* of larger diameter to provide a second catalyst bed 21*b* of larger diameter.

A first drying gas may be fed to the upper drying zone 14 through an upper drying zone inlet 18. The drying zone inlet 18 may be at an outlet end 24*a* of a pipe 24 for feeding the first drying gas stream to a center of the catalyst stream 20 as defined by the passageway 19*b* at the elevation of the drying zone inlet 18. A horizontal segment of the pipe 24 may enter through a side 34 of the vessel 10 and turn vertically upwardly to provide the terminal end and inlet 18. Typically, the center of the catalyst stream 20 will be located at the center of the reduction vessel 10, but it is most important that the first drying gas be distributed to the center of the cross sectional shape of the catalyst stream 20 in the catalyst bed 21b defined by the second passageway 19b at an elevation of the drying zone inlet 18. As shown in the FIGURE, the second catalyst bed 21b is cylindrical, so the first drying gas is distributed to the center of the circle defined by the second passageway 20b at the elevation of the drying zone inlet 18. The pipe 24 has the outlet end 24a directed upwardly. In an embodiment the outlet end 24a is directed into a cap 26.

The cap 26 may be hollow and have a closed upper end 27 and an open lower end 28. The cap 26 may comprise a wall 30 that is inclined. Preferably, the wall 30 that is inclined is an upper wall of the cap 26 to provide the closed upper end 27 and facilitate downward movement of the catalyst stream 20 by which catalyst particles slide down the inclined wall 30. The inclined wall 30 may have an included angle which is equal to the vertical shear angle of the catalyst particles. In an aspect the cap 26 may be conical in shape. Moreover, the cap 26 may be located at an elevation that is at least partially even with the elevation of the first annular baffle 22. Consequently, the cap 26 penetrates the catalyst stream 20 in the catalyst bed 21b that is defined by the second passageway 19b below the first annular baffle 22.

The first drying gas from the upper drying zone inlet 18 may be fed into a center of the catalyst stream 20 into a center of the cap 26. In an aspect, the first drying gas may be fed into the center of the cap 26 located in a center of the passageway 21b in the center of the reduction vessel 10. The first drying gas entering the cap 26 cannot proceed upwardly through the closed upper end 27, so the first drying gas must exit the cap downwardly through the open bottom end 28, reverse direction and flow upwardly around lower edges of the cap to contact the downwardly flowing catalyst stream 20 in the second catalyst bed 21b defined by the second passageway 19b.

The first drying gas contacts the catalyst stream 20 to desorb the water on the catalyst particles. Preferably, the first drying gas stream has sufficiently low moisture concentration to reduce the chemisorbed water on the catalyst in the catalyst stream 20 by at least 25 wt % compared to the moisture content of the catalyst stream 20 before entering the upper drying zone 14. The catalyst stream 20 flows downwardly through the upper drying zone 14 to provide sufficient time for the catalyst to be dried. The catalyst stream 20 contacts the first drying gas stream counter-currently. The catalyst will have an average residence time in the upper drying zone 14 of between 0.5 and 3 hours, with a preferred time between 1 and 2 hours. At least about 25 wt % of the totally chemisorbed water on the catalyst is removed in the drying zone 14.

The first drying gas is cycled through a upper drying zone 14 using a first blower for circulation of the drying gas. The first drying gas may also be cycled using a compressor. The first drying gas may include hydrogen. However, it is also contemplated that the drying gas may include $N_2$, Ar, He, $C_1$, $C_2$, $C_3$, $CO_2$, or air. The first drying gas is heated to a drying temperature before passing it to the upper drying zone 14 as the first drying gas stream. The first drying gas exits the reduction vessel 10 through the upper drying gas outlet 32. The upper drying zone temperature may be between 280° C. and 550° C., with a preferable temperature between 300° C. and 450° C. The pressure for the first reduction zone may be between 2 psig to 50 psig and a thermal mass ratio of the first drying gas stream may be between 0.8 and 5.

The first drying gas stream contacts the catalyst stream 20 to dry the catalyst stream that is flowing downwardly to provide a contacted or dried catalyst stream 20a and a wet gas stream. The wet gas stream is discharged from the drying gas outlet 32 in a side 34 of the vessel 10. The drying gas outlet 32 is at about the same elevation as the annular outer baffle 22. Consequently, after contacting the catalyst stream 20 to desorb water on the catalyst, the wet drying gas enters an annular region 36 outwardly of the baffle 22 adjacent to the drying gas outlet 32 and exits the drying gas outlet 32 from the reduction vessel 10.

An outer boundary of a passageway provides an enlarged inner diameter to allow the contacted catalyst stream 20a to spread out below the outer baffle 22 and provide a second catalyst bed 21b of wider diameter. However, an inner boundary of the catalyst bed 21b defined by the cap 26 may also widen inversely to the depth of the bed 21b due to an increasing diameter of the inclined wall 30 of the cap 26. The area of the top 25 of the second catalyst bed 21b defined by the annular spacing between the outer wall 34 and a lower end of the outer baffle 22 should be sufficient to discourage entrainment of catalyst particles from the bed 21b and into the drying gas outlet 32.

An advantage of the catalyst reduction process is that drying and reduction of the catalyst in separate zones 14, 16 can effectively remove the water with minimal hydrothermal damage, while keeping the reduction vessel size minimal. The present subject matter includes a lower reduction zone 16 where a separate reduction gas is used to complete the reduction process and to further reduce the chemisorbed water on the catalyst.

The dried catalyst stream 20a is further processed and flows from the upper drying zone 14 to the lower reduction zone 16, where the catalyst is contacted with a second reduction gas stream for reducing the valence state of metals on the catalyst and further drying the residual water. The second reduction gas enters through the lower reduction zone inlet 48 and is cycled through the lower reduction zone 16 optionally using a second blower for circulation of the reduction gas. The second reduction gas may also be cycled using a compressor. The second reduction gas may be made up of hydrogen. However it is also contemplated that the second reduction gas may include $C_1$, $C_2$, or $C_3$. The second reduction gas is heated to a reduction temperature before passing to the lower reduction zone 16 as the second reduction gas stream. The second reduction gas exits the reduction vessel 10 through the reducing gas outlet 58. The second reduction temperature is between 400° C. and 650° C., with a preferable temperature between 450° C. and 550° C. The pressure for the second reduction zone is between 2 psig to 50 psig and thermal mass ratio of the second reduction gas stream is between 0.8 and 5.

Below the first annular baffle 22 and the first inlet pipe 24 may be provided a second annular baffle 40. The second annular baffle may comprise an inclined, annular wall 40a and a vertical annular wall 40b. The second annular baffle 40 cooperates with a cone 42 disposed in the middle of the vessel 10 to provide an annular funnel 44 below the cap 26. The cone 42 may have the same height and be horizontally aligned with the inclined wall 40a. The annular funnel 44 defines a third passageway 19c. The vertical wall 40b defines a cylindrical wall that is concentric and horizontally aligned with an inner cylindrical wall 42a that depends from the cone 42. The annular, vertical wall 40b and the inner cylindrical wall 42a define an annular passage 46 therebetween. The annular funnel 44 consolidates the contacted, dried catalyst stream 20a from the second catalyst bed 21b into a third catalyst bed 21c defined by the third passageway 19c and directs catalyst from the third catalyst bed into the annular passage 46. The third catalyst bed 21c may be annular. The dried catalyst stream 20a descends through the annular passage 46 and is released from the lower end of the annular passage 46 to annularly distribute the dried catalyst stream 20a from a lower end of the annular passage 46 into an annularly noded third catalyst bed 21d defined by a fourth passageway 19d. The second annular baffle 40 and the cone 42 may be impermeable to catalyst and vapor flow or permeable to vapor flow.

The dried catalyst stream 20a in the fourth catalyst bed 21d is contacted with a second, reducing gas stream to reduce the valence state of a metal on the catalyst and provide a twice contacted or reduced catalyst stream 20b. The used second gas stream is discharged from the reducing vessel 10 through the reducing gas outlet 58.

In an aspect, a second gas or a reduction gas may be fed to the lower reduction zone 16 through a lower reduction zone inlet 48. The reduction zone inlet 48 may be at the outlet end 50a of a pipe 50 for feeding a second gas stream to a center of the dried catalyst stream 20a. A horizontal segment of the pipe 50 may enter through a side 34 of the vessel 10 and turn vertically upwardly to provide the outlet end 50a and inlet 48. Typically, the center of the fourth catalyst bed 21d will be the center of the vessel 10, but it is most important that the second reduction gas be distributed to the center of the cross sectional shape of the dried catalyst stream 20a in the fourth catalyst bed 21d defined by the passageway 19d at an elevation of the reduction zone inlet 48. The pipe 50 has the outlet end 50a directed upwardly. In an embodiment the outlet end 50a is directed into an optional second cap 52.

The second cap 52 may be hollow and have a closed upper end 53 and an open lower end 54. The cap 52 may comprise a wall 56 that is inclined. Preferably, the wall 56 that is inclined is an upper wall of the cap 52 to provide the closed upper end 53 and facilitate downward movement of the dried catalyst stream 20a by which catalyst particles slide down the inclined wall 56. In an aspect, the cap 52 may be conical in shape. Moreover, the cap 52 may be located at an elevation that is at least partially even with the elevation of the second annular baffle 40 and/or the annular passage 46. Consequently, the cap 52 penetrates the catalyst stream 21c that is consolidated by the annular passage 46.

The second reduction gas from the lower reduction zone inlet 48 may be fed into a center of the dried catalyst stream 20a into a center of the cap 52. The second reduction gas enters the cap 52 and cannot proceed upwardly through the a closed upper end 53, so the second reduction gas must exit the cap 52 downwardly through the open bottom end 54, reversing direction and flowing upwardly around lower edges of the cap to contact the downwardly flowing dried catalyst stream 20a that has been consolidated into the bed 21d.

The second reduction gas stream contacts the dried catalyst stream 20a to reduce the valence state of metals on the catalyst stream that is flowing downwardly to provide a twice contacted or a reduced catalyst stream 20b and a used gas stream. The used gas stream is discharged from the reducing gas outlet 58 in a side 34 of the vessel 10. The reducing gas outlet 58 is at about the same elevation as the annular outer baffle 40. Consequently, after contacting the catalyst stream, the used reducing gas enters an annular region 60 located outwardly of the baffle 40 and adjacent to the reducing gas outlet 58 and exits from the vessel 10. An outer boundary of the twice contacted catalyst stream 20b is allowed to spread out below the baffle 40 to provide a wider fourth catalyst bed 21d. However, the inner boundary of the fourth catalyst bed 21d may also widen due to a diameter of the inclined wall 56 of the cap 52 that increases inversely to depth. The area of the top 55 of the fourth catalyst bed 21d defined by the spacing between the outer wall 34 and a lower end of the second annular baffle 40 should be sufficient to discourage entrainment of catalyst particles from the fourth catalyst bed 21d and into the reducing gas outlet 58.

The used, second, reducing gas distributed into the fourth catalyst bed 21d may ascend into a space below the cone 42. At least one pipe 61 is provided through the annular passage 46 to provide communication between the space below the cone 42 and the annular region 60 outside of the second annular baffle 40. A plurality of pipes 61 may be spaced around the annular passage 46 at equal angular intervals to allow the used, second reducing gas to escape from below the cone 42 to the annular region 60. Used reducing gas is discharged from the reducing zone 16 through the reducing gas outlet 58.

A bottom cone 62 may be provided below the second reduction zone inlet 48 of the reducing zone 16 to direct reduced, regenerated catalyst to exit at least one catalyst outlet 64 from the vessel 10. A plurality of catalyst outlets 64 may be spaced around the cone 62 at equal angular intervals to facilitate catalyst exit from the vessel 10. The reduced catalyst stream may be transported in a line 68 to a reactor 70 to catalyze a chemical reaction such as a dehydrocyclodimerization reaction.

The second reduction zone 16 is operated and sized to allow for the catalyst to reside in the lower zone between 0.5 and 3 hours, with a preferred average residence time between 1 hours and 2 hours. The second reduction gas stream is sufficiently dry to reduce the chemisorbed water on the catalyst stream 20b by a maximum of about 75 wt % compared to the dried catalyst stream 20a before entering the second reduction zone 16. A maximum of about 75 wt % of the totally chemisorbed water on the catalyst stream 20 is removed in the second reduction zone 16.

Another advantage of this method of catalyst reduction process is that the separate zones may have temperature control of each inlet gas entering the individual zones. The first drying gas stream and the second reduction gas stream may include a common gas loop. For example, if the first drying gas stream and the second reduction gas stream include a common gas loop the first drying gas and second reduction gas streams may include the same temperature control, the same gas composition control, the same driers, or a mixture thereof. However, it is also contemplated that the first drying gas stream and the second reduction gas stream may have independent gas loops. For example, in this configuration the composition, temperature, and the drier system of the first drying gas stream and the second reduction gas stream may be independent.

Any suitable catalyst may be utilized such as at least one molecular sieve including any suitable material, e.g., alumino-silicate. The catalyst can include an effective amount of the molecular sieve, which can be a zeolite with at least one pore having a 10 or higher member ring structure and can have one or higher dimension. Typically, the zeolite can have a $Si/Al_2$ mole ratio of greater than 10:1, preferably 20:1-60:1. Preferred molecular sieves can include BEA, MTW, FAU (including zeolite Y and zeolite X), EMT, FAU/EMT intergrowth, MOR, LTL, ITH, ITW, MFI, MSE, MEL, MFI/MEL intergrowth, TUN, IMF, FER, TON, MFS, IWW, EUO, MTT, HEU, CHA, ERI, MWW, AEL, AFO, ATO, and LTA. Preferably, the zeolite can be MFI, MEL, WI/MEL intergrowth, TUN, IMF, MSE and/or MTW. Suitable zeolite amounts in the catalyst may range from 1-100%, and preferably from 10-90%, by weight.

Generally, the catalyst includes at least one metal selected from active metals, and optionally at least one metal selected from modifier metals. The total active metal content on the catalyst by weight is about less than 5% by weight. In some embodiments, the preferred total active metal content is less than about 3.0%, in yet in another embodiments the preferred total active metal content is less than 1.5%, still in yet in another embodiment the total active metal content on the catalyst by weight is less than 0.5 wt %. At least one metal is selected from IUPAC Groups that include 6, 7, 8, 9, 10, and 13. The IUPAC Group 6 trough 10 includes without limitation chromium, molybdenum, tungsten, rhenium, platinum, palladium, rhodium, iridium, ruthenium and osmium, zinc, copper, and silver. The IUPAC Group 13 includes without limitation gallium, indium. In addition to at least one active metal, the catalyst may also contain at least one modifier metal selected from IUPAC Groups 11-17. The IUPAC Group 11 trough 17 includes without limitation sulfur, gold, tin, germanium, and lead.

SPECIFIC EMBODIMENTS

While the following is described in conjunction with specific embodiments, it will be understood that this description is intended to illustrate and not limit the scope of the preceding description and the appended claims.

A first embodiment of the invention is a process of distributing gas into a catalyst stream comprising feeding a particulate stream downwardly in a vessel; feeding a gas stream into a center of the catalyst stream into a hollow cap; the gas stream entering the cap and exiting the cap and flowing upwardly to contact the catalyst stream that is flowing downwardly. An embodiment of the invention is one, any or all of prior embodiments in this paragraph up through the first embodiment in this paragraph further comprising discharging the gas stream from a side outlet in the vessel after contacting the catalyst stream. An embodiment of the invention is one, any or all of prior embodiments in this paragraph up through the first embodiment in this paragraph wherein the gas stream exits the cap through an open lower end. An embodiment of the invention is one, any or all of prior embodiments in this paragraph up through the first embodiment in this paragraph, wherein the catalyst stream has a minimum of 0.1 wt % chemisorbed water before contacting the gas stream and the catalyst stream is partially dried to have at least 25 wt % less chemisorbed water after contacting the gas stream than before contacting the gas stream. An embodiment of the invention is one, any or all of prior embodiments in this paragraph up through the first embodiment in this paragraph wherein the cap has an inclined side and particles of the catalyst stream slides down the inclined side. An embodiment of the invention is one, any or all of prior embodiments in this paragraph up through the first embodiment in this paragraph wherein the catalyst stream is consolidated into a cylindrical stream and the cap penetrates the cylindrical stream. An embodiment of the invention is one, any or all of prior embodiments in this paragraph up through the first embodiment in this paragraph wherein the gas stream is fed into the hollow cap through a pipe with an outlet end facing upwardly into the hollow cap. An embodiment of the invention is one, any or all of prior embodiments in this paragraph up through the first embodiment in this paragraph further comprising after contacting the catalyst stream with the gas stream comprising a first gas stream to provide a contacted catalyst stream, contacting the contacted catalyst stream with a second gas stream to provide a twice contacted catalyst stream and discharging the second gas stream from the vessel. An embodiment of the invention is one, any or all of prior embodiments in this paragraph up through the first embodiment in this paragraph wherein the second contacting step reduces the valence state of a metal on the catalyst in the contacted catalyst stream. An embodiment of the invention is one, any or all of prior embodiments in this paragraph up through the first embodiment in this paragraph wherein the contacted catalyst stream is consolidated into an annular stream before it is contacted with a second gas stream.

A second embodiment of the invention is an apparatus for distributing gas into a catalyst stream comprising an inlet for introducing a catalyst stream to a vessel; a pipe for feeding a gas stream to a center of a catalyst passageway, the pipe having an outlet end directed into a cap; a catalyst exit in a lower end of the vessel; and a gas outlet in a side of the vessel. An embodiment of the invention is one, any or all of prior embodiments in this paragraph up through the second embodiment in this paragraph wherein the cap has an open lower end. An embodiment of the invention is one, any or all of prior embodiments in this paragraph up through the second embodiment in this paragraph wherein the cap has a wall that is inclined. An embodiment of the invention is one, any or all of prior embodiments in this paragraph up through the second embodiment in this paragraph wherein the inclined wall is conical. An embodiment of the invention is one, any or all of prior embodiments in this paragraph up through the second embodiment in this paragraph further comprising an outer baffle comprising an inclined upper wall that is impermeable to gas flow and is at the same elevation as the outlet. An embodiment of the invention is one, any or all of prior embodiments in this paragraph up through the second embodiment in this paragraph wherein the outer baffle is a first outer baffle and further comprising a second outer baffle below the first outer baffle and a conical baffle that cooperates with the second outer baffle to provide an annular funnel below the cap. An embodiment of the invention is one, any or all of prior embodiments in this paragraph up through the second embodiment in this paragraph comprising a annular passage with a pipe extending through the annular passage to communicate a conical space under the conical baffle with an annular space outside of the second outer baffle. An embodiment of the invention is one, any or all of prior embodiments in this paragraph up through the second embodiment in this paragraph wherein the pipe for feeding a gas stream to the vessel comprises a first pipe, the gas stream comprises a first gas stream, the cap comprises a first cap, and the gas outlet in the side of the vessel comprises a first gas outlet; and further comprising a second pipe having an outlet end directed into a second cap and a second gas outlet in the side of the vessel and the second outer baffle comprises an inclined upper wall that is impermeable to gas flow and is at the same elevation as the second gas outlet. A reduction process comprising feeding a catalyst stream comprising water downwardly in a vessel; feeding a first gas stream into a center of the catalyst stream into a hollow cap; the first gas stream entering the cap and exiting the cap and flowing upwardly to contact and dry the catalyst stream that is flowing downwardly to provide a dried catalyst stream and a wet gas stream; discharging the wet gas stream through a first side outlet from the vessel; feeding a second gas stream to the vessel to contact the dried catalyst stream to reduce the valence state of metals in the dried catalyst stream to provide a reduced catalyst stream and a used gas stream; discharging the reduced catalyst stream and the used gas stream from the vessel. An embodiment of the invention is one, any or all of prior embodiments in this paragraph up through the second embodiment in this paragraph wherein the cap is a first cap and further comprising feeding the second gas stream into a center of the vessel into a second cap and the second gas stream entering the second cap and exiting the second cap and flowing upwardly to contact and reduce metals on catalyst in the dried catalyst stream that is flowing downwardly to provide the reduced catalyst stream and the used gas stream.

A third embodiment of the invention is a process comprising feeding a catalyst stream comprising water downwardly in a vessel; feeding a first gas stream into a center of the catalyst stream into a hollow cap; the first gas stream entering the cap and exiting the cap and flowing upwardly to contact and dry the catalyst stream that is flowing downwardly to provide a dried catalyst stream and a wet gas stream; discharging the wet gas stream through a first side outlet from the vessel; feeding a second gas stream to the vessel to contact the dried catalyst stream to reduce the valence state of metals in the dried catalyst stream to provide a reduced catalyst stream and a used gas stream; discharging the reduced catalyst stream and the used gas stream from the vessel. An embodiment of the invention is one, any or all of prior embodiments in this paragraph up through the third embodiment in this paragraph wherein the cap is a first cap and further comprising feeding the second gas stream into a center of the vessel into a second cap and the second gas stream entering the second cap and exiting the second cap and flowing upwardly to contact and reduce metals on catalyst in the dried catalyst stream that is flowing downwardly to provide the reduced catalyst stream and the used gas stream.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A process of distributing gas into a catalyst stream comprising: feeding a catalyst stream downwardly in a vessel;
    feeding a gas stream into a center of said catalyst stream into a hollow cap;
    said gas stream entering said cap and exiting said cap and flowing upwardly to contact said catalyst stream that is flowing downwardly,
    wherein said catalyst stream has a minimum of 0.1 wt % chemisorbed water before contacting said gas stream and said catalyst stream is partially dried to have at least 25 wt % less chemisorbed water after contacting said gas stream than before contacting said gas stream.

2. The process of claim 1 further comprising discharging said gas stream from a side outlet in said vessel after contacting said catalyst stream.

3. The process of claim 1 wherein said gas stream exits said cap through an open lower end.

4. The process of claim 1 wherein said cap has an inclined side and particles of said catalyst stream slides down said inclined side.

5. The process of claim 1 wherein said catalyst stream is consolidated into a cylindrical stream and said cap penetrates said cylindrical stream.

6. The process of claim 1 wherein said gas stream is fed into said hollow cap through a pipe with an outlet end facing upwardly into said hollow cap.

7. The process of claim 6 further comprising after contacting the catalyst stream with said gas stream comprising a first gas stream to provide a contacted catalyst stream, contacting said contacted catalyst stream with a second gas stream to provide a twice contacted catalyst stream and discharging said second gas stream from said vessel.

8. The process of claim 7 wherein said second contacting step reduces the valence state of a metal on the catalyst in the contacted catalyst stream.

9. The process of claim 1 wherein said contacted catalyst stream is consolidated into an annular stream before it is contacted with a second gas stream.

10. A reduction process comprising:
    feeding a catalyst stream comprising water downwardly in a vessel;
    feeding a first gas stream into a center of said catalyst stream into a hollow cap; said first gas stream entering said cap and exiting said cap and flowing upwardly to contact and dry said catalyst stream that is flowing downwardly to provide a dried catalyst stream and a wet gas stream;
    discharging said wet gas stream through a first side outlet from said vessel;
    feeding a second gas stream to said vessel to contact said dried catalyst stream to reduce the valence state of metals in said dried catalyst stream to provide a reduced catalyst stream and a used gas stream; and
    discharging said reduced catalyst stream and said used gas stream from said vessel.

11. The process of claim 10 wherein said cap is a first cap and further comprising feeding said second gas stream into a center of said vessel into a second cap and said second gas stream entering said second cap and exiting said second cap and flowing upwardly to contact and reduce metals on catalyst in said dried catalyst stream that is flowing downwardly to provide said reduced catalyst stream and said used gas stream.

* * * * *